United States Patent
Dallerup Rasmussen et al.

(10) Patent No.: US 11,680,936 B2
(45) Date of Patent: *Jun. 20, 2023

(54) TAPE FOR BIOMARKER ANALYSIS OF A MILK SAMPLE

(71) Applicant: DELAVAL HOLDING AB, Tumba (SE)

(72) Inventors: Claus Dallerup Rasmussen, Tumba (SE); Thomas Nikolai Carlsen, Tumba (SE)

(73) Assignee: DeLaval Holding AB, Tumba (SE)

( * ) Notice: Subject to any disclaimer, the term of this patent is extended or adjusted under 35 U.S.C. 154(b) by 370 days.

This patent is subject to a terminal disclaimer.

(21) Appl. No.: 16/769,109

(22) PCT Filed: Dec. 18, 2018

(86) PCT No.: PCT/SE2018/051336
§ 371 (c)(1),
(2) Date: Jun. 2, 2020

(87) PCT Pub. No.: WO2019/132761
PCT Pub. Date: Jul. 4, 2019

(65) Prior Publication Data
US 2021/0231630 A1    Jul. 29, 2021

(30) Foreign Application Priority Data
Dec. 28, 2017 (SE) .................... 1751661-8

(51) Int. Cl.
*G01N 33/04* (2006.01)
*G01N 35/00* (2006.01)

(52) U.S. Cl.
CPC ....... *G01N 33/04* (2013.01); *G01N 35/00009* (2013.01)

(58) Field of Classification Search
CPC .. G01N 33/04; G01N 33/14; G01N 35/00009; G01N 35/00019; G01N 2021/7759
(Continued)

(56) References Cited

U.S. PATENT DOCUMENTS

| 6,372,515 B1 | 4/2002 | Casterlin et al. |
| 2002/0124803 A1 | 9/2002 | Chen et al. |

(Continued)

FOREIGN PATENT DOCUMENTS

| CN | 1156251 A | 8/1997 |
| CN | 101316702 A | 12/2008 |

(Continued)

OTHER PUBLICATIONS

International Search Report and Written Opinion, dated Apr. 24, 2019, from corresponding PCT application No. PCT/SE2018/051336.

(Continued)

*Primary Examiner* — Maureen Wallenhorst
(74) *Attorney, Agent, or Firm* — Nixon & Vanderhye

(57) ABSTRACT

A tape (170) includes a bottom film (410), upon which dry sticks (180*a*, 180*b*, 180*c*) are separately arranged, which dry sticks (180*a*, 180*b*, 180*c*) are configured to indicate at least one biomarker value of a milk sample of an animal (100); and a top film (310) covering the plurality of dry sticks (180*a*, 180*b*, 180*c*), the top film (310) being arranged on the bottom film (410), the top film (310) being arranged to be peeled off an individual dry stick (180*a*, 180*b*, 180*c*) before application of the milk sample to the dry stick (180*a*, 180*b*, 180*c*).

19 Claims, 3 Drawing Sheets

(58) Field of Classification Search
USPC ........ 422/400, 402, 403, 420, 430, 68.1, 66, 422/74; 436/20, 22, 23, 44, 164, 169
See application file for complete search history.

(56) References Cited

U.S. PATENT DOCUMENTS

| | | |
|---|---|---|
| 2006/0260939 A1 | 11/2006 | Anderson et al. |
| 2007/0144922 A1* | 6/2007 | Imoarai ............ G01N 33/54386 206/204 |
| 2012/0273112 A1 | 11/2012 | Dagenbach et al. |
| 2014/0135606 A1 | 5/2014 | Yasui |
| 2015/0328632 A1 | 11/2015 | Kurata et al. |
| 2016/0313319 A1 | 10/2016 | Titmus et al. |
| 2017/0016876 A1 | 1/2017 | Samproni |
| 2019/0082659 A1 | 3/2019 | Mottram |
| 2020/0337262 A1* | 10/2020 | Dallerup Rasmussen ................... G01N 33/04 |
| 2021/0148941 A1* | 5/2021 | Dallerup Rasmussen ................... G01N 35/00009 |
| 2021/0231629 A1* | 7/2021 | Carlsen ................ G01N 33/558 |

FOREIGN PATENT DOCUMENTS

| | | |
|---|---|---|
| CN | 105699668 A | 6/2016 |
| CN | 106574225 A | 4/2017 |
| WO | 2004/034063 A1 | 4/2004 |
| WO | 2017/144913 A1 | 8/2017 |
| WO | 2017/184621 A1 | 10/2017 |

OTHER PUBLICATIONS

SE Search Report, dated Aug. 6, 2018, from corresponding SE application No. 1751661-8.

Yu et al., "Inline Progesterone Monitoring in the Dairy Industry", Cell Press, 2017, pp. 579-582, vol. 35, No. 7.

Office Action issued in Chinese Patent Application No. 201880079308.6 dated Jul. 4, 2022.

\* cited by examiner

TAPE FOR BIOMARKER ANALYSIS OF A MILK SAMPLE

TECHNICAL FIELD

This document discloses a tape. More particularly, a tape is described, for holding dry sticks measuring at least one biomarker value of a milk sample of an animal.

BACKGROUND

On an animal farm, it is important to keep the animals healthy in order to enhance milk/meat production. For example, it is important to inseminate animals at an optimal moment in order to successfully fertilise the cow. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

Thereby, a farmer/operator is provided with important information concerning each individual animal. However, to perform and analyse biomarker measurements of all individual animals at a farm, e.g. by applying milk samples on prepared dry sticks, and analyse these samples are time consuming for the farmer. It also put high demands on administrative skills on the farmer to distinguish biomarker measurements from different animals; as well as high demands on cleanliness for not allowing a biomarker measurement of a first animal to be contaminated by biological matters of another animal.

It would for these reasons be advantageous for the farmer, if the taking of biomarker measurements on milk samples of different animals could be automated, and thereby minimising or at least reducing the manual work effort of the farmer.

It would be desired to find a way to assist the farmer in analysing his/her animals and enhance production at the farm, relieving him/her from the tedious work of handling a plurality of individual dry sticks which are prepared for detecting biomarker measurements.

SUMMARY

It is therefore an object of this invention to solve at least some of the above problems and facilitate for an operator to measure a biomarker value of a milk sample of an animal.

According to a first aspect of the invention, this objective is achieved by a tape. The tape comprises a bottom film, and a top film. On the bottom film, dry sticks are separately arranged. These dry sticks are configured to indicate at least one biomarker value of a milk sample of an animal. The top film is configured to cover the dry sticks, which are arranged on the bottom film. Also, the top film is configured to be peeled off an individual dry stick before application of the milk sample to the dry stick.

A biomarker, or biological marker, generally refers to a measurable indicator of some biological state or condition of the animal. The biomarker value measurement may be associated with pregnancy/reproduction of the animal.

By keeping the dry sticks separate from each other on the bottom film and cover them with the top film, the unused dry sticks are protected from contamination from milk of other animals than the animal to be tested, but also from affection of humidity from the environment, moisture in the air, and various impurities that may appear in an agricultural environment. By peeling off the top film from the next dry stick to be used for testing, automatically, the operator is provided with a convenient solution for making biomarker value measurement with a minimum of required user effort, enabling biomarker value measurements also on a farm having a shortage of operators, and without requiring any particular involvement or skill of the operator.

In a first possible implementation of the tape according to the first aspect, the dry sticks may be arranged on the bottom film with an inclination in relation to an axis, orthogonal to a longitudinal axis of the tape, of at least 10 degrees.

By arranging the dry sticks on the bottom film with the inclination, it becomes easier to peel off the top film from the bottom film, and expose the subsequent dry stick to be used for testing.

In a second possible implementation of the tape according to the first aspect, or according to the first possible implementation thereof, the bottom film may comprise a bottom layer, a medium layer and a top layer.

By dividing the bottom film into different layers, different materials with different properties may be selected for the different layers, leading to improved tape characteristics.

In a third possible implementation of the tape according to the first aspect, or according to any previously disclosed possible implementation thereof, the top film may comprise a bottom layer, a medium layer and a top layer.

In a fourth possible implementation of the tape according to the first aspect, or according to any previously disclosed possible implementation thereof, the bottom layer and the top layer of the bottom film and/or the top film may be made of plastic while the medium layer may be made of aluminium.

The aluminium of the medium layers provide stability to the tape, but also protects the dry sticks from humidity by forming a fluid barrier, while the plastic of the bottom layers and the top layers provide protection of the aluminium layer from mechanical impacts and decrease friction of the tape surface, leading to a smoother running of the tape. The plastic of the top layer of the bottom film and the bottom layer of the top film also enable welding around each dry stick.

In a fifth possible implementation of the tape according to the first aspect, or according to any previously disclosed possible implementation thereof, the top layer of the bottom film may be made of polyethylene.

Polyethylene may be utilised with particular advantage in order to weld a seal around each dry stick on the tape.

In a sixth possible implementation of the tape according to the first aspect, or according to any previously disclosed possible implementation thereof, the bottom layer of the top film may be made of polyethylene, polyamide, polyethylene terephthalate, polyethylene terephthalate polyester.

In a seventh possible implementation of the tape according to the first aspect, or according to any previously disclosed possible implementation thereof, a seal may be created around each separately arranged dry stick by a welded seam, created between the top layer of the bottom film and the bottom layer of the top film.

In an eighth possible implementation of the tape according to the first aspect, or according to any previously disclosed possible implementation thereof, the medium layer of the top film may be thinner than the medium layer of the bottom film.

By using a thinner aluminium medium layer of the top film, more tape could be rolled onto a tape spool, without losing the desired stability enhancing features of the thicker medium layer of the bottom film.

In a ninth possible implementation of the tape according to the first aspect, or according to any previously disclosed possible implementation thereof, the medium layer of the bottom film and/or the top film may have a thickness between about 9 μm-25 μm.

In a tenth possible implementation of the tape according to the first aspect, or according to any previously disclosed possible implementation thereof, each separately arranged dry stick may be sealed individually by a welded seam. The sealed dry sticks are arranged at a distance from each other.

Thereby the unused dry sticks are protected from undesired moisture, humidity, dirt and mechanical damages, until they are to be used and the top film is peeled off, resulting in more reliable measurement values.

In an eleventh possible implementation of the tape according to the first aspect, or according to any previously disclosed possible implementation thereof, the tape comprises an opening, arranged between the welded seams of at least some of the dry sticks on the bottom film, configured to enable liquid transport during cleaning.

Thanks to the aperture configured to receive a liquid evacuator at the rear part of the cassette, superfluous liquid, e.g. from rinsing of the needle applying the milk samples, between milk samples from different animals, could be collected and conveyed out of the cassette. Thereby, the risk of carrying over from a milk sample of a first animal, to a milk sample of a second animal is reduced.

Milk of a first animal may contaminate a milk sample of another, subsequently tested animal. To avoid contamination, or carry over, the tubings and the needle may be flushed with milk of the animal to be tested before the milk sample is applied to the dry stick. For avoiding that the flushed milk of the animal to be tested soaks and/or contaminate other unused dry sticks, the flushing may be made through the opening of the tape, e.g. by lowering the needle through the opening, and capture the flushed milk with a liquid evacuator. The liquid evacuator may then via a tube convey liquid away from the cassette.

In a twelfth possible implementation of the tape according to the first aspect, or according to any previously disclosed possible implementation thereof, the bottom film may comprise a reference mark, configured to assist a camera in finding the dry stick.

Thanks to the reference mark, the camera may find the dry stick easier and faster than without any reference mark, leading to that a shorter time has to be spent on each test sampling, thereby enhancing the efficiency of the biomarker value measurement.

In a thirteenth possible implementation of the twelfth possible implementation of the tape according to the first aspect, the reference mark may be configured to assist the camera in adjusting peel off of the top film, from the dry stick.

Thereby, thanks to the reference mark, the top film may be peeled off sufficiently for enabling application of the milk sample to the dry stick, but not so much that the top film is peeled off the neighbour dry stick. Thereby, the neighbour dry stick remains protected by the top film during the application of the milk sample to the preceding dry stick.

In a fourteenth possible implementation of the tape according to the first aspect, or according to any previously disclosed possible implementation thereof, at least the bottom film of the tape may comprise a first group of advancement apertures, arranged at a first edge of the tape; and a second group of advancement apertures, arranged at a second edge of the tape.

An advantage of the advancement apertures arranged at the edges of the tape is that a capstan reel comprising teeth may engage with advancement apertures of the tape and thereby adjust the position of the tape.

In a fifteenth possible implementation of the tape according to the first aspect, or according to any previously disclosed possible implementation thereof, the tape may be configured to be rolled on a spool.

In a sixteenth possible implementation of the tape according to the first aspect, or according to any previously disclosed possible implementation thereof, the tape may comprise about 400-600 dry sticks.

Hereby, enough dry sticks are provided on a tape of a cassette to last for about a month, when used in conjunction with a milking robot serving about 60-70 animals.

Thanks to the described aspects, biomarker values of milk samples of animals on the farm may be measured in an automatised manner, requiring a minimum of efforts of an operator.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a tape, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
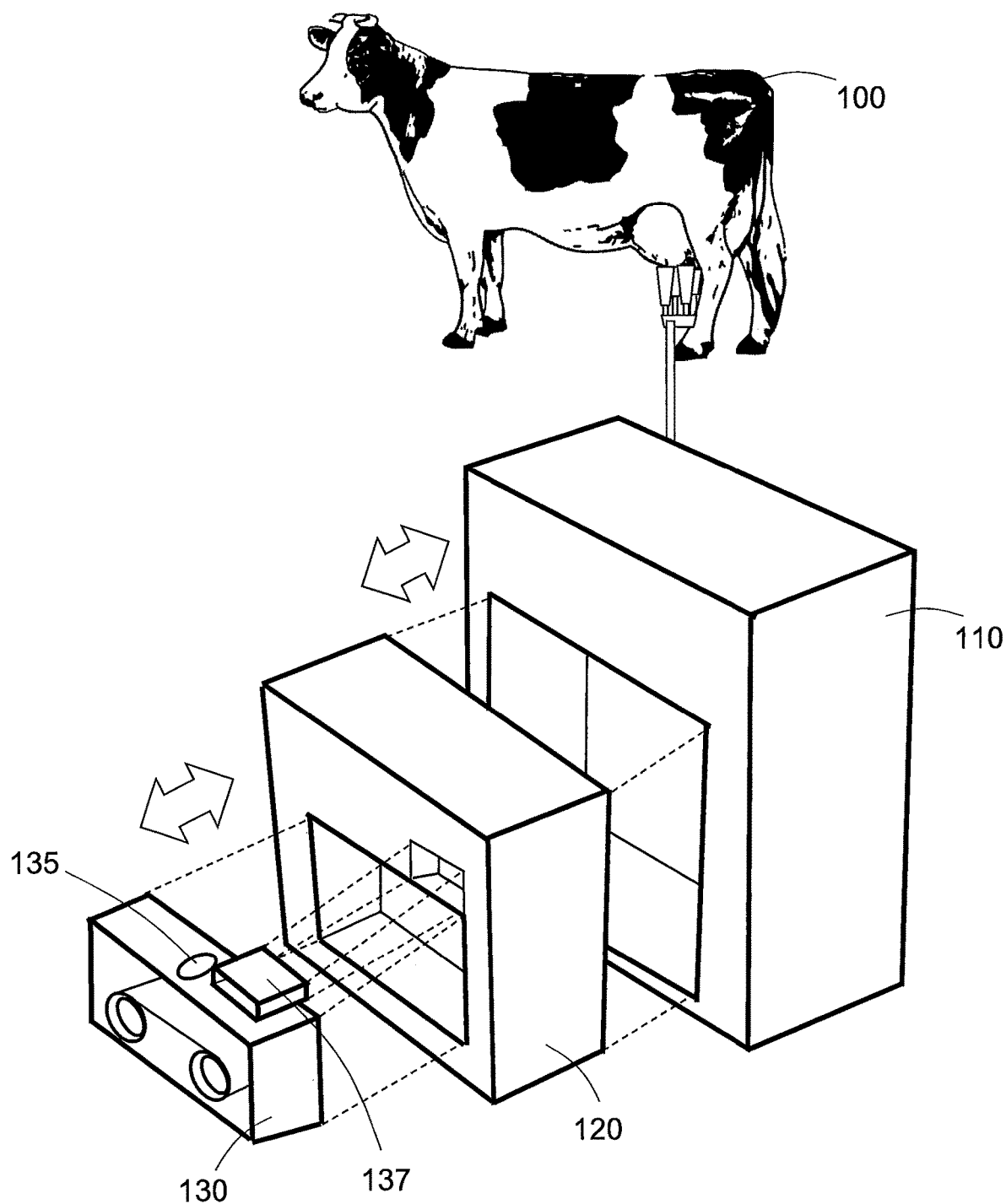
FIG. 1 illustrates an example of an arrangement for measuring a biomarker value of a milk sample of an animal.

FIG. 1 illustrates a scenario with an animal 100 which may be comprised in a herd of dairy animals at a dairy farm.

"Animal" may be any arbitrary type of domesticated female milk producing and/or meat producing mammal such as cow, goat, sheep, horse, camel, dromedary, primate, dairy buffalo, donkey, reindeer, yak, etc.

Milk of the animal 100 may be extracted by a milking equipment such as e.g. a milking robot or other milking arrangement, and provided to a service module 120.

The service module 120 may be releasably inserted into the milking equipment in some embodiments. Thus, there may be an interface between the milking equipment and the service module 120 for providing milk and possibly electricity via the milking equipment to the service module 120.

The service module 120 comprises various electronics and equipment such as a camera, one or several pumps, a tube element for attachment to the interface to the milking equipment, motors, a communication unit etc.

A cassette 130 may be detachably inserted into the service module 120. The cassette 130 comprises a tape with dry sticks, configured to indicate a biomarker value of a milk sample of the animal 100. The cassette 130 may in some embodiments be configured to be detachably inserted in the service module 120 and held in place by a fastening means such as a snap lock, a magnet, a screw, etc., and a door of the service module 120 may be closed for enclosing the cassette 130 within the service module 120, thereby further fixating the cassette 130 in the position.

Thereby, a milk sample of the animal 100 may be extracted from the animal 100 by the milking equipment and provided via the service module 120 to one of the dry sticks on the tape of the cassette 130. The dry sticks may react on presence and/or amount of one or several biomarkers, e.g. by changing colours, or intensity of a colour. The camera in the service module 120 may capture an image through an opening 135 in the cassette 130. The captured image of the dry stick may then be analysed by a control unit, and based on the intensity of the colour, presence and/or quantity of the biomarker in the milk sample may thereby be determined.

The measured biomarker may be e.g. progesterone, glycoprotein, oestrogen and/or Gonadotropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrus and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the operator to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the operator may subscribe to a cassette 130 comprising a certain dry stick on the tape configured to measure a biomarker, or a set of biomarkers, as selected by the farmer; and/or different cassettes 130 comprising dry sticks on the tape configured to measure different biomarkers, or sets of biomarkers, during different periods of time of the year.

In some embodiments, a dosing module 137 may also be detachably inserted into the service module 120. The dosing module 137 may comprise for example a needle, and/or one or several pumps. A diluent container with diluent may be external to the dosing module 137.

Figure 2A:
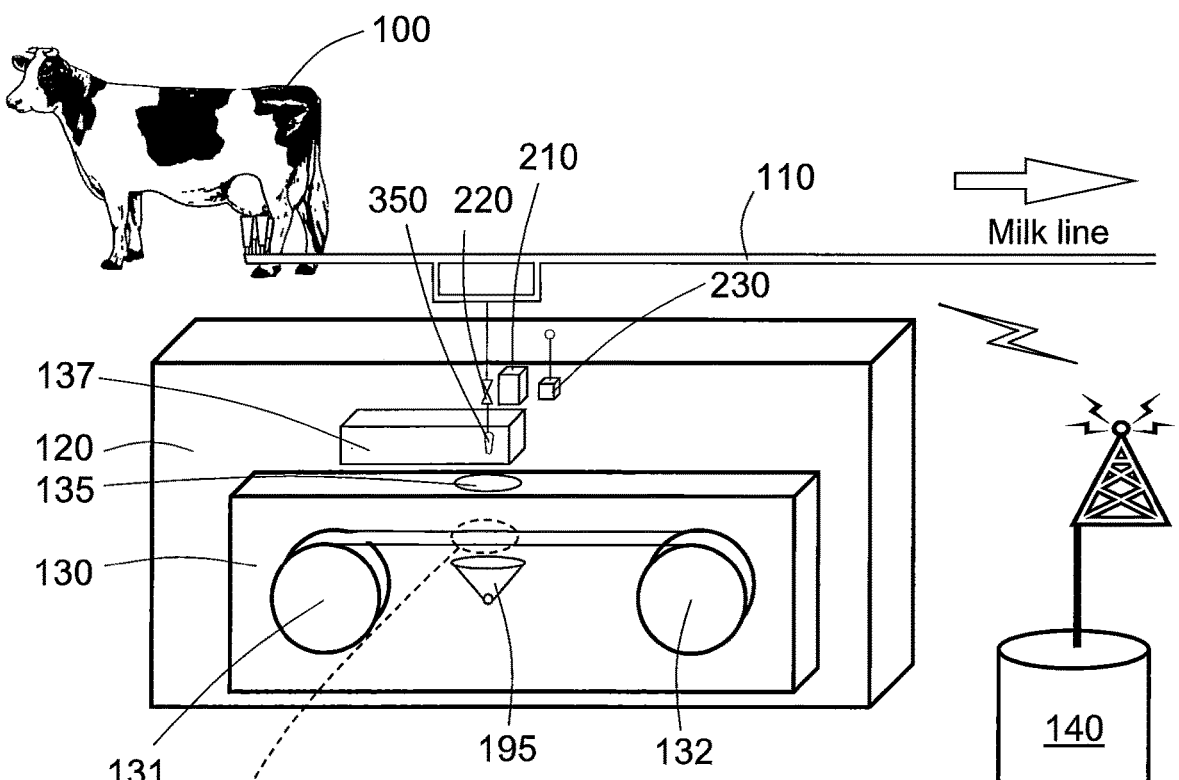
FIG. 2A illustrates a cassette inserted into a service module, according to an embodiment.

FIG. 1 and FIG. 2A depict general overviews of the environment in which the tape according to the provided solution is intended to operate, without going too much into details, in order for the reader to get a rough overview. Sublime examples of details of the involved entities, in particular the cassette 130 and the tape, and how they interact with each other may be fully enjoyed in FIG. 2B, FIG. 3, and FIG. 4.

FIG. 2A illustrates a scenario illustrating a service module 120, a cassette 130, and a dosing module 137, according to an embodiment. The service module 120 comprises electronics and equipment such as e.g. a camera 210, a tube element 220 for attachment to the milking equipment, a motor, a communication unit 230, etc., to be used for determining a biometric value of a milk sample received from an animal 100. In some embodiments, the dosing module 137 may comprise one or several pumps configured to act on the tube element 220 for advancing the milk sample through the tube element 220.

In the illustrated embodiment, the dosing module 137 may comprise a needle 350 for applying the milk sample to a dry stick 180a, 180b, 180c on a tape 170 in the cassette 130 through an opening 135 in the cassette 130. The camera 210 may then align the needle 350 with the dry stick 180a, 180b, 180c on the tape 170 of the cassette 130.

The camera 210 of the service module 120 may capture an image of the dry sticks 180a, 180b, 180c of the carrier tape 170 through the opening 135, and based on these images, a cassette external motor may adjust the tape 170 for positioning a new dry sticks 180a, 180b, 180c, on which a new test is to be made, in relation to the needle 350.

The communication unit 230 may communicate via a wired or wireless communication interface, with a control unit 150, a database 140, and/or an output unit 160.

Such wireless communication interface may comprise, or at least be inspired by wireless communication technology such as Wi-Fi, 3GPP LTE, Bluetooth (BT) to name but a few possible examples of wireless communications in some embodiments.

The camera 210 of the service module 120 is configured to inspect one dry stick 180a, 180b, 180c on the tape 170 of the cassette 130, through the opening 135 of the cassette 130. The camera 210 may also assist in alignment of the needle 350 and the position of the dry stick 180a, 180b, 180c on the tape 170, by adjusting the tape 170.

Further, the service module 120 also comprises a tube element 220 configured to receive the milk sample of the animal 100 via a milking equipment and provide the milk sample to a needle 350, i.e. the needle 350 comprised in the dosing module 137

The dosing module 137 may in addition comprise at least one pump in some embodiments, configured to act on the tube element 220 for providing the milk sample to the needle 350. The pump may thus act on the tube element 220 to get the milk sample to propagate through the tube element 220, to reach the needle 350; or the mixing chamber 355 of the needle 350. The mixing chamber 355 may alternatively be external to the needle 350.

The dosing module 137 may also comprise a liquid evacuator or drainage 195, which may collect liquid that has been output by the needle 350. The liquid, when comprising merely milk, may be returned back to the milk line in some embodiments. In other embodiments, when the milk has been mixed with diluent, the liquid may be conveyed away from the cassette 130 in order not to soak or contaminate other, unused, dry sticks 180a, 180b, 180c of the tape 170 on the cassette 130.

The control unit 150 is configured to determine a biomarker value of the milk sample of the animal 100, based on an analysis of the image, captured by the camera 210. The control unit 150 may be comprised in the service module 120 in some embodiments; or be external to the service module 120.

The database 140 may store measured biometric values of the animal 100, associated with an identity reference of the animal 100 and/or a time stamp of the measurement. Other measurements and/or data related to the animal 100 may also be stored in the database 140, such as milk yield, e.g. measured by the milk flow meter, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, an operator may take part of the result of the biomarker measurement of the milk sample. The operator is thereby able to analyse the status of the animal 100, such as e.g. if the animal 100 is in heat, in case progesterone is measured.

When a deviation, exceeding a first threshold limit, is detected between the outcomes of the biomarker measurement and the corresponding reference value, an alert may be outputted to the operator. The alert may comprise e.g. visual information, an audio message, a tactile signal or a combination thereof, encouraging the operator to further investigate the reasons for the detected deviation in result. In case a plurality of people is working with the herd, a broadcast may be made to the plurality of operators and their respective associated output units 160, in some embodiments.

Figure 2B:
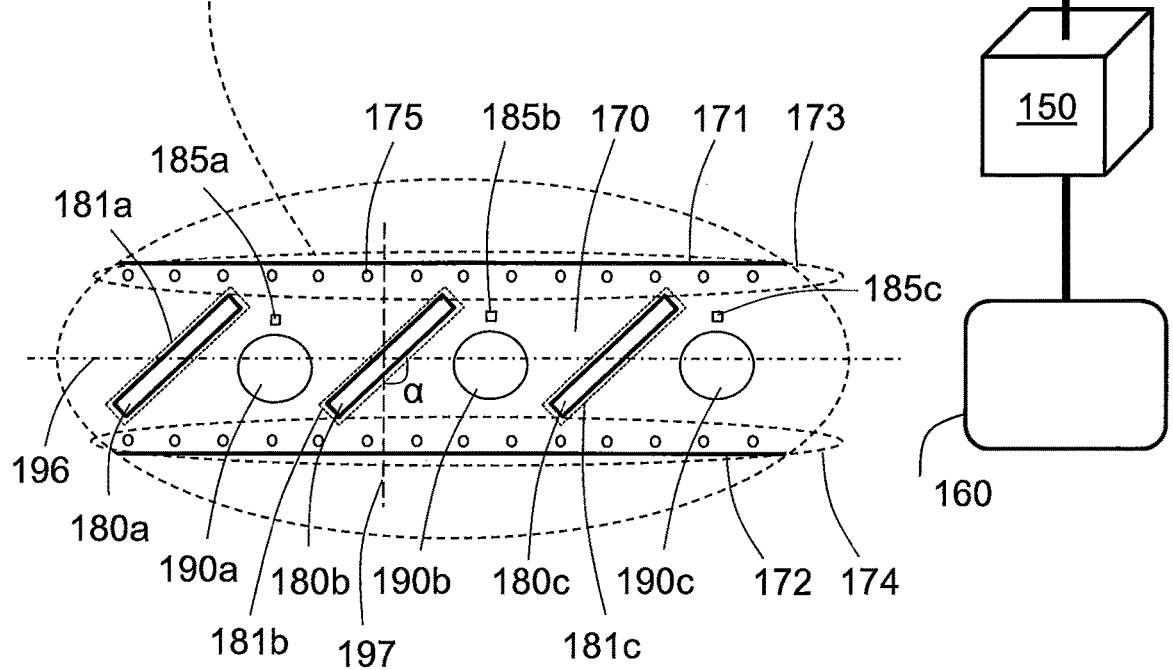
FIG. 2B illustrates a section of a tape comprising dry sticks, according to an embodiment.

FIG. 2B illustrates a tape 170 according to an embodiment. The cassette 130, which may be releasably inserted into the service module 120, comprises the tape 170, which in turn comprises a plurality of dry sticks 180a, 180b, 180c.

The dry sticks 180a, 180b, 180c may be arranged with an inclination a in relation to an axis 197, orthogonal to a longitudinal axis 196 of the tape 170. The inclination a may for example be 15 degrees or there about, or e.g. 10-30 degrees in some embodiments.

An opening 190a, 190b, 190c, may be arranged between at least some of the dry sticks 180a, 180b, 180c, on the tape 170, or on a bottom film of the tape 170, i.e. between the welded seams 181a, 181b, 181c of at least some of the dry sticks 180a, 180b, 180c on the bottom film. The opening 190a, 190b, 190c is configured to convey liquid away from the dry sticks 180a, 180b, 180c during cleaning, or before applying the milk sample to the dry stick 180a, 180b, 180c.

Milk of a first animal 100 may contaminate a milk sample of another, subsequently tested animal. To avoid contamination, or carry over, the tubings and the needle 350 may be flushed with milk of the animal to be tested before the milk sample is applied to the dry stick 180a, 180b, 180c. For avoiding that the flushed milk of the animal to be tested soaks and/or contaminate other unused dry sticks 180a, 180b, 180c, the flushing may be made through the opening 190a, 190b, 190c of the tape 170, e.g. by lowering the needle 350 through the opening 190a, 190b, 190c, and capture the flushed milk with a liquid evacuator 195. The liquid evacuator 195 may then via a tube convey liquid away from the cassette 130.

The tape 170, or the bottom film of the tape 170 may further comprise a reference mark 185a, 185b, 185c, configured to assist a camera 210 in finding the dry stick 180a, 180b, 180c. The reference mark 185a, 185b, 185c may comprise e.g. a hole, a colour mark, a barcode, a simple geometry, or similar.

The reference mark 185a, 185b, 185c may also assist the camera 210 in determining the advancement of the top film reel, to peel off the top film of the dry stick 180a, 180b, 180c, enough to enable application of the milk sample to the dry stick 180a, 180b, 180c, while not peeling off the top film of the next dry stick 180a, 180b, 180c.

Further, the tape 170, or the bottom film of the tape 170 may comprise a first group 173 of advancement apertures 175, arranged at a first edge 171 of the tape 170; and a second group 174 of advancement apertures 175, arranged at a second edge 172 of the tape 170, or the bottom film of the tape 170.

Each dry stick 180a, 180b, 180c may be separately arranged on the tape 170, or the bottom film of the tape 170, by a welded seam 181a, 181b, 181c, and wherein the sealed dry sticks 180a, 180b, 180c are arranged on a distance from each other.

Figure 3:
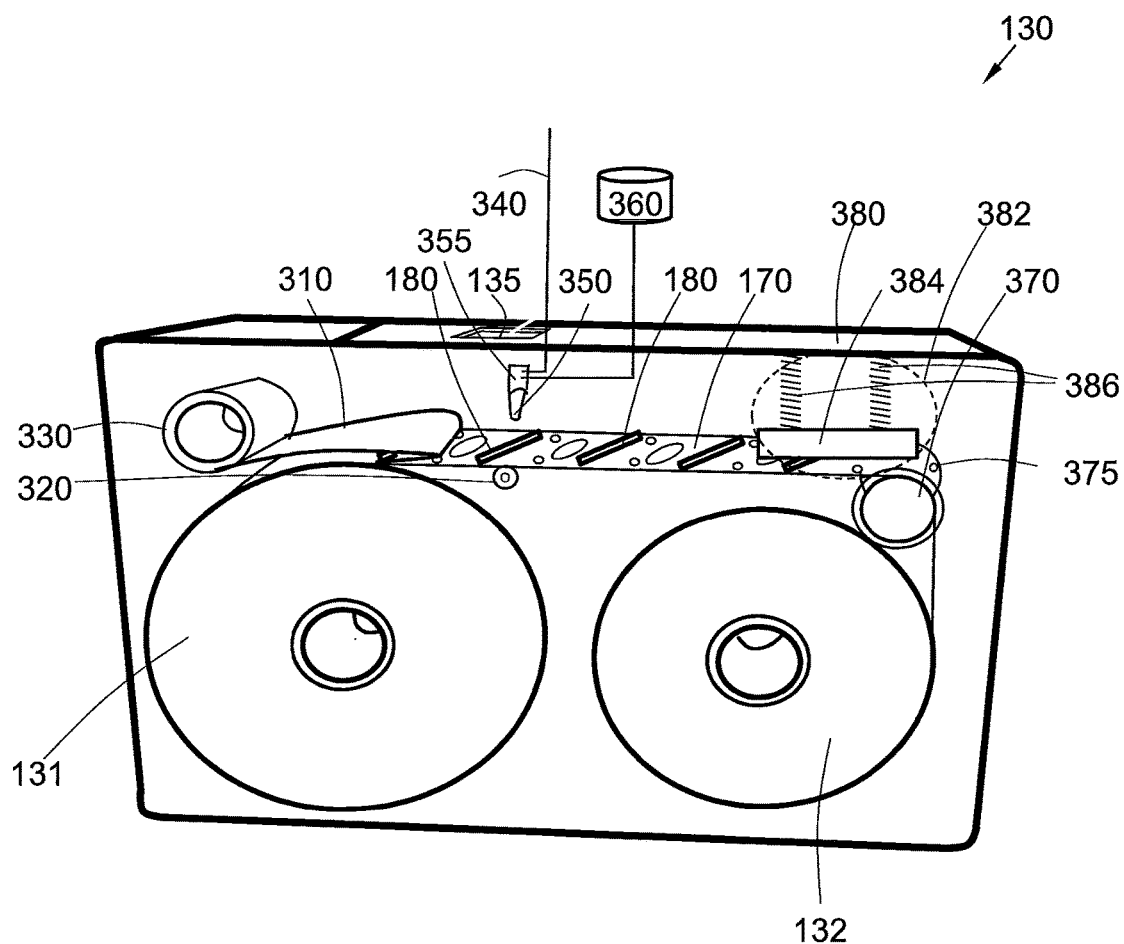
FIG. 3 illustrates a cassette, according to an embodiment.

FIG. 3 illustrates a cassette 130, comprising a tape 170 with dry sticks 180a, 180b, 180c separately, i.e. individually, arranged on the tape 170 at a distance from each other.

In the illustrated embodiment, the tape 170 comprises a bottom film, comprising the dry sticks 180a, 180b, 180c, covered with a top film 310 configured to seal the dry sticks 180a, 180b, 180c on the tape 170.

Also, in the illustrated embodiment, a top film reel 330 is comprised, arranged to peel off and collect the top film 310 of the tape 170. The top film 310 may be peeled off just before the milk sample is to be applied to the peeled off dry stick 180a, 180b, 180c.

Further, the cassette 130 may comprise a capstan reel 370 comprising teeth 375, for engaging with advancement apertures 175 on the tape 170.

The cassette 130 may in addition also comprise a top lid 380, comprising the opening 135, configured to enable the needle 350 of the service module 120 to be inserted for applying the milk sample of the animal 100 to one of the dry sticks 180a, 180b, 180c, to which the top film 310 has been peeled off.

The top lid 380 may comprise at least one pressure exertion member 382, arranged to act on the tape 170 to keep it at a predetermined distance from the top lid 380. Thereby, the camera 210 may be focused on the dry stick 180a, 180b, 180c, as they are constantly situated at the same distance from the camera 210. The pressure exertion member 382 may comprise a spring 386, or a flexible material, and a tape interface unit 384.

Also, the top lid 380 may act on the tape 170 to keep the advancement apertures 175 on the tape 170 in place at the teeth 375 on the capstan reel 370. The form of the top lid 380 may thus have a shape keeping the advancement apertures 175 on the tape 170 in place at the teeth 375 on the capstan reel 370.

Some embodiments of the cassette 130 may comprise a tape supporting member 320, arranged to guide the tape 170 in a trajectory between the tape distributing spool 131, and the capstan reel 370. The tape supporting member 320 may ascertain that the tape 170 is kept at the predetermined distance from the camera 210, thereby enabling the camera 210 to be focused on the dry stick 180a, 180b, 180c.

In some embodiments, the tape 170 may comprise e.g. 300-700 dry sticks 180a, 180b, 180c, or preferably about 400-600 dry sticks 180*a*, 180*b*, 180*c*. Thereby, the tape 170 of the cassette 130 may comprise enough dry sticks 180*a*, 180*b*, 180*c* for testing milk samples of an average automatic milking robot for about a month. The cassette 130 with the tape 170 and the dry sticks 180*a*, 180*b*, 180*c* may then be wasted and exchanged for another one, e.g. through a service subscription. In some embodiments, the cassette 130 may be recycled; i.e. the used cassette 130 may be opened and the used tape 170 may be removed from the used cassette 130. Then, a new, unutilised tape 170 with dry sticks 180*a*, 180*b*, 180*c* may be inserted into the cassette 130, and the cassette 130 may be reassembled.

The dry sticks 180*a*, 180*b*, 180*c* may be designed for one-time usage each. In some embodiments, the dry sticks 180*a*, 180*b*, 180*c* of the tape 170 may be configured to change colour or colour nuance when exposed to the biomarker.

The camera 210 in the service module 120 may capture an image of the dry sticks 180*a*, 180*b*, 180*c* in question, after a predetermined or configurable time period. The colour, or colour intensity of the dry stick 180*a*, 180*b*, 180*c* on the captured image may then be analysed by the control unit 150, where different colour intensities may be associated with a certain biomarker level of the milk sample.

The milk sample may in some embodiments be mixed with a diluent before being applied to the dry sticks 180*a*, 180*b*, 180*c* on the tape 170, e.g. in the mixing chamber 355.

In embodiments, wherein the diluent is kept in a separate container 360 in a separate entity, the operator may change the cassette 130, the dosing module 137, and/or the diluent container 360 at different time intervals. In a non-limiting example, the cassette 130 may be changed once a month while the dosing module 137 comprising the needle 350 may be changed twice a year. In some embodiments, the diluent container 360 may be changed e.g. every second month, every third month, etc. In some embodiments, the operator may refill the diluent, which may reduce overall costs of the operator. Yet an advantage by having multiple replaceable entities such as the cassette 130, the dosing module 137, the diluent container 360, etc., is that in case a fabrication error or a transportation damage occur of a therein comprised entity, such as e.g. the needle 350, only that particular replaceable entity (cassette 130, dosing module 137, diluent container 360, etc.) comprising the defect entity has to be exchanged, which saves resources.

In some embodiments, the dosing module 137 may comprise at least one pump configured to act on the tube element 220 for providing the milk sample to the needle 350; and a second pump configured to provide diluent to a mixing chamber 355.

The ratio of milk and diluent may be adjusted by changing the respective pump speed of one or both liquids, i.e. milk/diluent respectively, in case each liquid is associated with a respective pump.

The needle 350 comprised in the dosing module 137 may comprise the mixing chamber 355 configured to mix obtained diluent with the milk sample before applying the mixed milk sample to the one dry stick 180*a*, 180*b*, 180*c*, in some embodiments. Alternatively, the milk and the diluent may be mixed in a separate mixing chamber 355 in some embodiments.

In some embodiments, the cassette 130 and/or the dosing module 137 may be sealed from the environment and thereby create a climate chamber, wherein a climate environment prevails in the cassette 130/dosing module 137. The cassette 130/dosing module 137 thereby becomes isolated from environmental impact of dust, dirt, liquids, etc., of the farm.

When the tape 170 is moved for placing the dry stick 180*a*, 180*b*, 180*c* to be used in position aligned with the needle 350, the milk/diluent mix may be applied on the dry stick 180*a*, 180*b*, 180*c*.

An advantage of the disclosed solution, by making a division between a service module 120 comprising camera, motor, pumps and other electronics and/or apparatuses; and one or several cassettes or modules 130, 137, 360 comprising disposable material, the solution becomes very easy to use for the operator.

The cassette 130 may comprise dry sticks 180*a*, 180*b*, 180*c* etc., for supporting the farm for a certain predetermined period of time, such as e.g. a month, two months, etc. Before the end of that time period, a supplier may provide a new cassette 130 to the farm, which the operator easy may put into the service module 120, without having to interact with the sensible electronics of the service module 120. The used cassette 130 may then be disposed.

In case a hardware failure or other malfunction occur, the operator may remove the service module 120 from the milking equipment (and also remove the cassette 130 from the service module 120) and provide the service module 120 to a service supplier for reparation/adjustment. During the time period the service module 120 is on repair, the operator may borrow another service module 120 from the service supplier, for example. Thereby, biomarker values of the animals 100 may be determined without interruptions, also when the service module 120 or any part thereof is malfunctioning. Also, as no external technician is required to visit the farm, neither for changing the disposable cassette 130, or the dosing module 137, nor for analysing errors in the service module 120, costs for service and maintenance are minimised or at least reduced.

Figure 4:
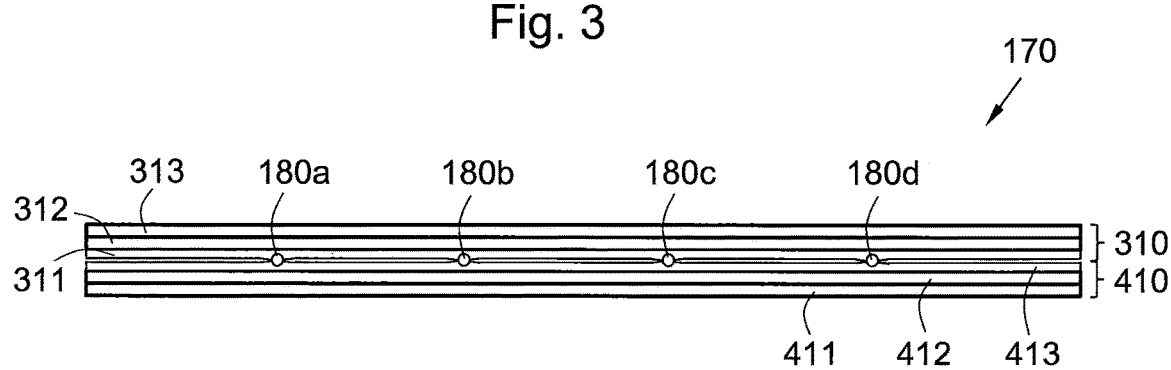
FIG. 4 illustrates a cross section of a tape comprising dry sticks, according to an embodiment.

FIG. 4 illustrates a cross section of a tape 170 according to an embodiment. The tape 170 comprises a bottom film 410, operable to hold a plurality of dry sticks 180*a*, 180*b*, 180*c*, separately on the bottom film 410, which dry sticks 180*a*, 180*b*, 180*c* are configured to indicate at least one biomarker value of a milk sample of an animal 100. Each dry stick 180*a*, 180*b*, 180*c* may be individually sealed by a welded seam 181*a*, 181*b*, 181*c*, arranged at a distance from each other.

Further, the tape 170 also comprises a top film 310 configured to cover the plurality of dry sticks 180*a*, 180*b*, 180*c* on the bottom film 410, and to be peeled off an individual dry stick 180*a*, 180*b*, 180*c* before application of the milk sample to the dry stick 180*a*, 180*b*, 180*c*.

A top film reel 330 of the cassette 130 may be arranged to peel off and collect the top film 310 of the tape 170.

The reason for applying the top film 310 is that it is important that milk from a first animal 100 does not soak the dry stick 180*a*, 180*b*, 180*c* on which a subsequent animal is to use for biomarker test, as the milk from the first animal may contaminate the dry stick 180*a*, 180*b*, 180*c* of the second animal. For this reason, the cassette 130 may further comprise a desealer, configured to remove the sealing tape from the one dry stick 180*a*, 180*b*, 180*c* when the one dry stick 180*a*, 180*b*, 180*c* is adjusted into a position aligned with the needle 350. The top film 310 may be thinner than the bottom film 410 in some embodiments, such as e.g. 10% thinner, 20% thinner, 40% thinner, etc.

The bottom film 410 may comprise a bottom layer 411, a medium layer 412 and a top layer 413. The bottom layer 411 and the top layer 413 may be made of plastic, like e.g.

polyethylene, polypropylene, polyamide, polyethylene terephthalate, polyethylene terephthalate polyester, polychlorotrifluoro ethylene, polyvinylidene chloride, polypropylene, polyvinyl chloride and/or polystyrene or similar material such as a thermoplastic polyester. In particular, the top layer 413 may be made of polyethylene. In some embodiments, the plastic may comprise bioplastic, or green plastic, i.e. comprise a plastic material which is degradable, biodegradable, and/or compostable.

The medium layer 412 of the bottom film 410 may be made of aluminium or an aluminium based alloy, and e.g. have a thickness between 9 μm-25 μm.

The top film 310 of the tape 170 comprise a bottom layer 311, a medium layer 312 and a top layer 313. The bottom layer 311 and the top layer 313 may be made of plastic, like e.g. polyethylene, polypropylene, polyamide, polyethylene terephthalate, polychlorotrifluoro ethylene, Polyvinylidene chloride, polypropylene, polyvinyl chloride and/or polystyrene or similar material. In particular, the bottom layer 311 may with advantage be made of polyethylene. In some embodiments, the plastic may comprise bioplastic, or green plastic, i.e. comprise a plastic material which is degradable, biodegradable, and/or compostable.

The layers 411, 412, 413 of the bottom film 410; and the layers 311, 312, 313 of the top film 310, respectively, may be laminated.

The medium layer 312 of the top film 310 may be made of aluminium or an aluminium based alloy, and e.g. have a thickness between 9 μm-25 μm.

Using a thin layer of aluminium foil, e.g. around 9 μm, for medium layer 412 of the bottom film 410 and/or the medium layer 312 of the top film 310 has the advantage of allowing more (longer) tape 170 on the spools 131, 132 of the cassette 130. It is also cheaper than using a thick (i.e. around 25 μm) aluminium foil. However, using a thick aluminium foil for the medium layers 412, 312 makes the tape 170 less sensible to mechanical damage. A compromise may be to use a thick aluminium foil, such as about e.g. 15-25 μm for the medium layer 412 of the bottom film 410 and a thinner aluminium foil (e.g. about 9-15 μm) for the medium layer 312 of the top film 310, in some embodiments.

The dry sticks 180a, 180b, 180c may be maintained between the bottom film 410 and the top film 310, and be individually sealed. The individual sealing of each dry stick 180a, 180b, 180c may be made by welding the top layer 413 of the bottom film 410 together with the bottom layer 311 of the top film 310. Thereby, the dry sticks 180a, 180b, 180c are very well protected from milk stain, or humidity that may affect the operation of the dry sticks 180a, 180b, 180c, when they are not in turn to receive the milk sample from the needle 350. In order to facilitate the welding, the top layer 413 of the bottom film 410 and/or the bottom layer 311 of the top film 310 may be made of polyethylene, as polyethylene is easy to weld.

The purpose of the medium layers 312, 412 is to provide firmness to the tape 170, while yet allowing the tape 170 to be flexible enough to be rolled on the spools 131, 132 of the tape 170. For this purpose, the medium layers 312, 412 with advantage may be made of aluminium foil; or a foil made of an aluminium alloy. Also, the medium layers 312, 412 provide liquid barriers, protecting the dry sticks 180a, 180b, 180c from humidity.

The purpose of the bottom layer 411 of the bottom film 410 is to protect the medium layer 412 from scratches and other undesired mechanical impact, as the medium layer 412, in particular when made of aluminium foil, is fragile and sensitive for scratches. The same may be said about the top layer 313 of the top film 310. The bottom layer 411 of the bottom film 410 and the top layer 313 of the top film 310 may with advantage be made of plastic as mentioned above. The plastic also has the advantage of low friction, which ascertain a smooth running of the tape 170 when being distributed between the spools 131, 132 of the tape 170.

The embodiments, or parts thereof, illustrated in FIG. 1, FIG. 2A, FIG. 2B, FIG. 3, and/or FIG. 4 may with advantage be combined with each other for achieving further benefits.

The terminology used in the description of the embodiments as illustrated in the accompanying drawings is not intended to be limiting of the described tape 170, cassette 130, service module 120, and/or control unit 150. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

The invention claimed is:

1. A tape (170) comprising:
   dry sticks (180a, 180b, 180c) configured to indicate at least one biomarker value of a milk sample of an animal (100);
   a bottom film (410), upon which the dry sticks (180a, 180b, 180c) are separately arranged;
   a top film (310) that covers the dry sticks (180a, 180b, 180c), the top film (310) being arranged on the bottom film (410); and
   a seal around each said dry stick (180a, 180b, 180c), each said seal being provided between the bottom film (410) and the top film (310),
   wherein the seal around each said dry stick (180a, 180b, 180c) is a respective welded seam (181a, 181b, 181c) that individually seals each said dry stick,
   wherein the dry sticks (180a, 180b, 180c), sealed by the respective welded seams, are arranged at a distance from each other,
   the top film (310) being peelable to be peeled off an individual dry stick (180a, 180b, 180c) before application of the milk sample to an individual one of the dry sticks (180a, 180b, 180c) with each unused ones of said individual dry stick (180a, 180b, 180c) not yet having application of the milk sample remaining on the bottom film and being covered by the top film (310) during the application of the milk sample to said individual one of the dry sticks (180a, 180b, 180c) such that the top film (310) protects the unused ones of the dry sticks (180a, 180b, 180c) from moisture, humidity, dirt, and mechanical damages until use.

2. The tape (170) according to claim 1, wherein the dry sticks (180a, 180b, 180c) are arranged on the bottom film (410) with an inclination (α) in relation to an axis (197), orthogonal to a longitudinal axis (196) of the tape (170), of at least 10 degrees.

3. The tape (170) according to claim 1, wherein the bottom film (410) comprises a bottom layer (411), a medium layer (412), and a top layer (413).

4. The tape (170) according to claim 3, wherein the top film (310) comprises a bottom layer (311), a medium layer (312), and a top layer (313).

5. The tape (170) according to claim 4, wherein the bottom layer (311, 411) and the top layer (313, 413) of the bottom film (410) and/or the top film (310) are made of plastic while the medium layer (312, 412) is made of aluminium.

6. The tape (170) according to claim 4, wherein the bottom layer (311) of the top film (310) is made of polyethylene, polyamide, polyethylene terephthalate, or polyethylene terephthalate polyester.

7. The tape (170) according to claim 4, wherein each said welded seam (181a, 181b, 181c) is between the top layer (413) of the bottom film (410) and the bottom layer (311) of the top film (310) and the welded seam is comprised of the top layer (413) of the bottom film (410) and the bottom layer (311) of the top film (310), and adjacent ones of the welded seam are separated by a region where the top layer (413) of the bottom film (410) and the bottom layer (311) of the top film (310) are adjacent each other and not welded together.

8. The tape (170) according to claim 7, wherein the bottom layer (411) and the top layer (413) of the bottom film (410) are made of plastic and the medium layer (412) of the bottom film (410) is made of aluminium.

9. The tape (170) according to claim 4, wherein the medium layer (312) of the top film (310) is thinner than the medium layer (412) of the bottom film (410).

10. The tape (170) according to claim 4, wherein the medium layer (312, 412) of at least one of the bottom film (410) and the top film (310) has a thickness between 9 μm-25 μm.

11. The tape (170) according to claim 3, wherein the top layer (413) of the bottom film (410) is made of polyethylene.

12. The tape (170) according to claim 1, comprising:
an opening (190a, 190b, 190c) arranged between the welded seams (181a, 181b, 181c) of at least some of the dry sticks (180a, 180b, 180c), each said opening being on the bottom film (410), each said opening being configured to convey liquid away from the dry sticks (180a, 180b, 180c) during cleaning.

13. The tape (170) according to claim 1, wherein the bottom film (410) comprises a reference mark (185a, 185b, 185c), configured to assist a camera (210) in finding each said dry stick (180a, 180b, 180c).

14. The tape (170) according to claim 13, wherein the reference mark (185a, 185b, 185c) is configured to assist the camera (210) in adjusting peel off of the top film (310), from each said dry stick (180a, 180b, 180c).

15. The tape (170) according to claim 1, wherein at least the bottom film (410) of the tape (170) comprises:
a first group (173) of advancement apertures (175), arranged at a first edge (171) of the tape (170); and
a second group (174) of advancement apertures (175), arranged at a second edge (172) of the tape (170).

16. The tape (170) according to claim 1 rolled on a spool (131, 132).

17. The tape (170) according to claim 1, comprising from 400 to 600 of said dry sticks (180a, 180b, 180c).

18. The tape (170) according to claim 1, further comprising:
an opening (190a, 190b, 190c) arranged between at least some of the dry sticks (180a, 180b, 180c), each said opening being on the bottom film (410), each said opening being configured to convey liquid away from the dry sticks (180a, 180b, 180c) during cleaning.

19. A tape (170) comprising:
dry sticks (180a, 180b, 180c) configured to indicate at least one biomarker value of a milk sample of an animal (100);
a bottom film (410), upon which the dry sticks (180a, 180b, 180c) are separately arranged;
a top film (310) that covers the dry sticks (180a, 180b, 180c), the top film (310) being arranged on the bottom film (410); and
a seal around each said dry stick (180a, 180b, 180c), each said seal being provided between the bottom film (410) and the top film (310),
wherein the seal around each said dry stick (180a, 180b, 180c) is a respective welded seam (181a, 181b, 181c) that individually seals each said dry stick,
wherein the dry sticks (180a, 180b, 180c), sealed by the respective welded seams, are arranged at a distance from each other, and wherein the dry sticks (180a, 180b, 180c) are arranged on the bottom film (410) with an inclination (α) in relation to an axis (197), orthogonal to a longitudinal axis (196) of the tape (170), of at least 10 degrees.

* * * * *